(12) United States Patent
Mishima et al.

(10) Patent No.: US 6,840,925 B2
(45) Date of Patent: Jan. 11, 2005

(54) THROWAWAY WEARING ARTICLE FOR DISPOSAL OF BODILY DISCHARGES

(75) Inventors: Yoshitaka Mishima, Kagawa-ken (JP); Takamitsu Igaue, Kagawa-ken (JP)

(73) Assignee: Uni-Charm Corporation, Ehime-ken (JP)

(*) Notice: Subject to any disclaimer, the term of this patent is extended or adjusted under 35 U.S.C. 154(b) by 13 days.

(21) Appl. No.: 10/101,025

(22) Filed: Mar. 19, 2002

(65) Prior Publication Data

US 2002/0138058 A1 Sep. 26, 2002

(30) Foreign Application Priority Data

Mar. 21, 2001 (JP) ........................................ 2001-081605

(51) Int. Cl.[7] .............................................. A61F 13/15
(52) U.S. Cl. .......................... 604/385.01; 604/385.01; 604/385.19
(58) Field of Search .................. 604/385.01, 385.03, 604/385.08, 385.09, 385.101, 385.13, 385.24, 327, 355, 346–348, 353, 385.19, 317

(56) References Cited

U.S. PATENT DOCUMENTS

| | | | | |
|---|---|---|---|---|
| 719,811 A | * | 2/1903 | Kent ........................... | 604/348 |
| 976,883 A | * | 11/1910 | Keagy ......................... | 604/354 |
| 3,194,238 A | * | 7/1965 | Breece, Jr. .................. | 604/329 |
| 3,532,093 A | * | 10/1970 | Lovret ......................... | 604/348 |
| 4,813,943 A | * | 3/1989 | Smith .......................... | 604/329 |
| 4,846,820 A | * | 7/1989 | Jensen ......................... | 604/339 |
| 4,886,508 A | * | 12/1989 | Washington ................. | 604/327 |
| 4,968,312 A | * | 11/1990 | Khan ..................... | 604/385.13 |
| 5,004,463 A | * | 4/1991 | Nigay .......................... | 604/329 |
| 5,342,583 A | * | 8/1994 | Son ............................. | 422/107 |
| 5,618,279 A | * | 4/1997 | Pudlo .................... | 604/385.09 |
| 6,007,524 A | * | 12/1999 | Schneider ................... | 604/327 |
| 6,133,501 A | * | 10/2000 | Hallock et al. ............. | 604/369 |
| 6,346,097 B1 | * | 2/2002 | Blaney ........................ | 604/327 |
| 6,402,729 B1 | * | 6/2002 | Boberg et al. ......... | 604/385.28 |
| 6,464,673 B1 | * | 10/2002 | Ben Natan ............. | 604/385.01 |
| 6,527,756 B1 | * | 3/2003 | Mishima et al. ....... | 604/385.19 |
| 2002/0072726 A1 | * | 6/2002 | Mishima et al. ....... | 604/385.22 |

FOREIGN PATENT DOCUMENTS

WO    WO 99/00092    1/1999

* cited by examiner

*Primary Examiner*—John J. Calvert
*Assistant Examiner*—Michele Kidwell
(74) *Attorney, Agent, or Firm*—Butzel Long

(57) ABSTRACT

A throwaway wearing article for disposal of bodily discharges improved so that a cylindrical guide for bodily discharge can be brought in close contact with a zone surrounding the anus without use of an adhesive. A flat bag-like receptacle is formed on its upper sheet with an inlet means having the cylindrical guide adapted to guide bodily discharge such as loose passage into a receptacle. An elastically stretchable supporting member extending under extension between front and rear sections of the receptacle is operatively associated with a peripheral edge of the upper end of the cylindrical guide.

6 Claims, 7 Drawing Sheets

THROWAWAY WEARING ARTICLE FOR DISPOSAL OF BODILY DISCHARGES

BACKGROUND OF THE INVENTION

This invention relates to a throwaway wearing article suitable for disposal of feces, particularly disposal of loose passage.

WO No. 99/00092 discloses a wearing article for disposal of feces in a form of a bag. This bag has an opening and a flange surrounding the opening wherein the flange is coated on its upper surface with self-adhesive. This bag is adapted to be used in an integral combination with a disposable diaper and, when wearing the diaper, the bag is placed upon inside the disposable diaper and the flange is adhesively fixed around anus.

However, the bag of well known art as has been cited above is disadvantageous in that an attempt to ensure sufficiently high adhesive force of the flange may cause the wearer to experience a pain as the flange is peeled off from the wearer's skin or the self-adhesive may cause an eruption of the wearer's skin.

SUMMARY OF THE INVENTION

It is an object of this invention to provide a throwaway wearing article provided with a bag for disposal of bodily discharges such as loose passage improved so that the bag can be held in close contact with the wearer's skin without use of self-adhesive.

According to this invention, there is provided a throwaway wearing article for disposal of bodily discharges comprising a body facing upper sheet, a garment facing lower sheet and an elongate flat bag composed of a front section formed on a side of a wearer's belly and a rear section formed on a side of said wearer's back wherein said upper sheet is formed with a cylindrical guide means adapted to guide bodily discharges into the bag.

The cylindrical guide means further has a lower end contiguous to an opening formed in the upper sheet and an upper end lying above the upper sheet so that the cylindrical guide means may be stretched and contracted in a vertical direction between these upper and lower ends, the bag being provided with an elastic member extending under tension between the front and rear sections above the upper sheet, and the elastic member being operatively associated with a peripheral edge of the upper end of the guide means so that contraction of the elastic member causes the guide means to be stretched upward as the wearing article is curved longitudinally of the bag with the upper sheet inside.

DETAILED DESCRIPTION OF THE PREFERRED EMBODIMENTS

Details of a throwaway wearing article for disposal of bodily discharges according to this invention will be more fully understood from the description of the embodiment in a form of loose passage disposal means given hereinafter in reference to the accompanying drawings.

Figure 1:
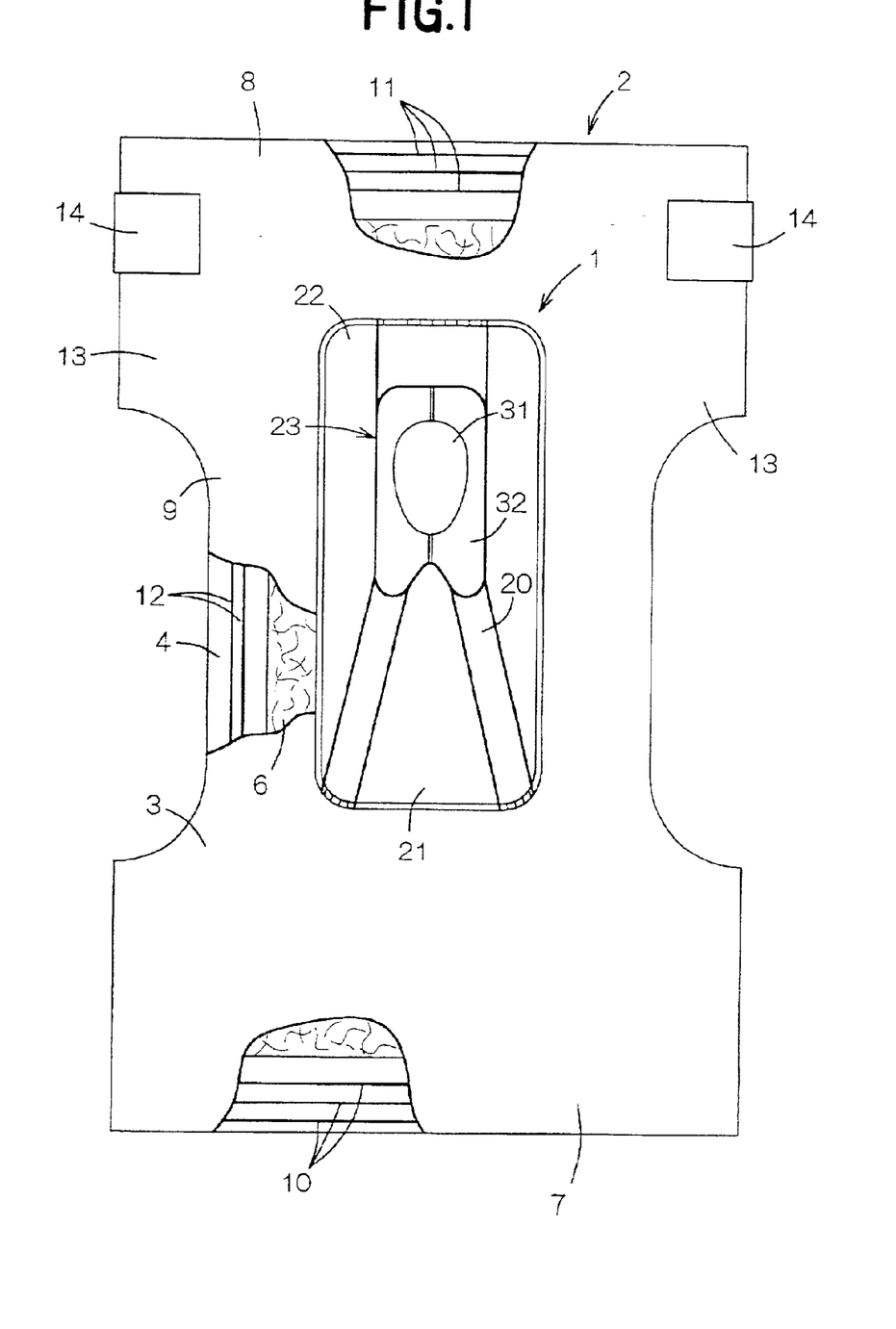
FIG. 1 is a partially cutaway plan view showing a wearing article for disposal of bodily discharges placed upon a disposable diaper.

FIG. 1 is a partially cutaway plan view showing a loose passage disposal means 1 placed upon the inside of a disposable diaper 2 as an garment which is adapted to be used in combination with this loose passage disposal means 1 and developed together in a flat state. The diaper 2 shown as partially cutaway is of well known art and comprises a liquid-pervious topsheet 3, a liquid-impervious backsheet 4 and a liquid-absorbent core 6 interposed between these two sheets 3,4. The diaper 2 is provided along its longitudinally front and rear ends 7,8 extending in a circumferential direction of the trunk and along its transversely opposite side edges 9 extending in the circumferential direction of respective legs with elastic members 10, 11 associated with a waist-hole and elastic members 12 associated with a pair of leg-holes. These elastic members 10, 11, 12 are secured under tension to the inner surface of at least one of the top- and backsheets 3,4. The diaper 2 is further provided on transversely opposite side edges 13 of its rear trunk region with tape fasteners 14.

The disposal means 1 is formed in a rectangle shape which is elongate in back-and-forth direction (i.e., in vertical direction as viewed in FIG. 1). The disposal means 1 has front and rear sections 21, 22 and the rear section 22 is formed in its transversely middle zone with a loose passage inlet 23. The disposal means 1 may be worn in combination with the diaper 2 so that the front section 21 is placed on the inside of the front trunk region of the diaper 2 and the loose passage inlet 23 is placed against a zone surrounding the anus.

Figure 2:
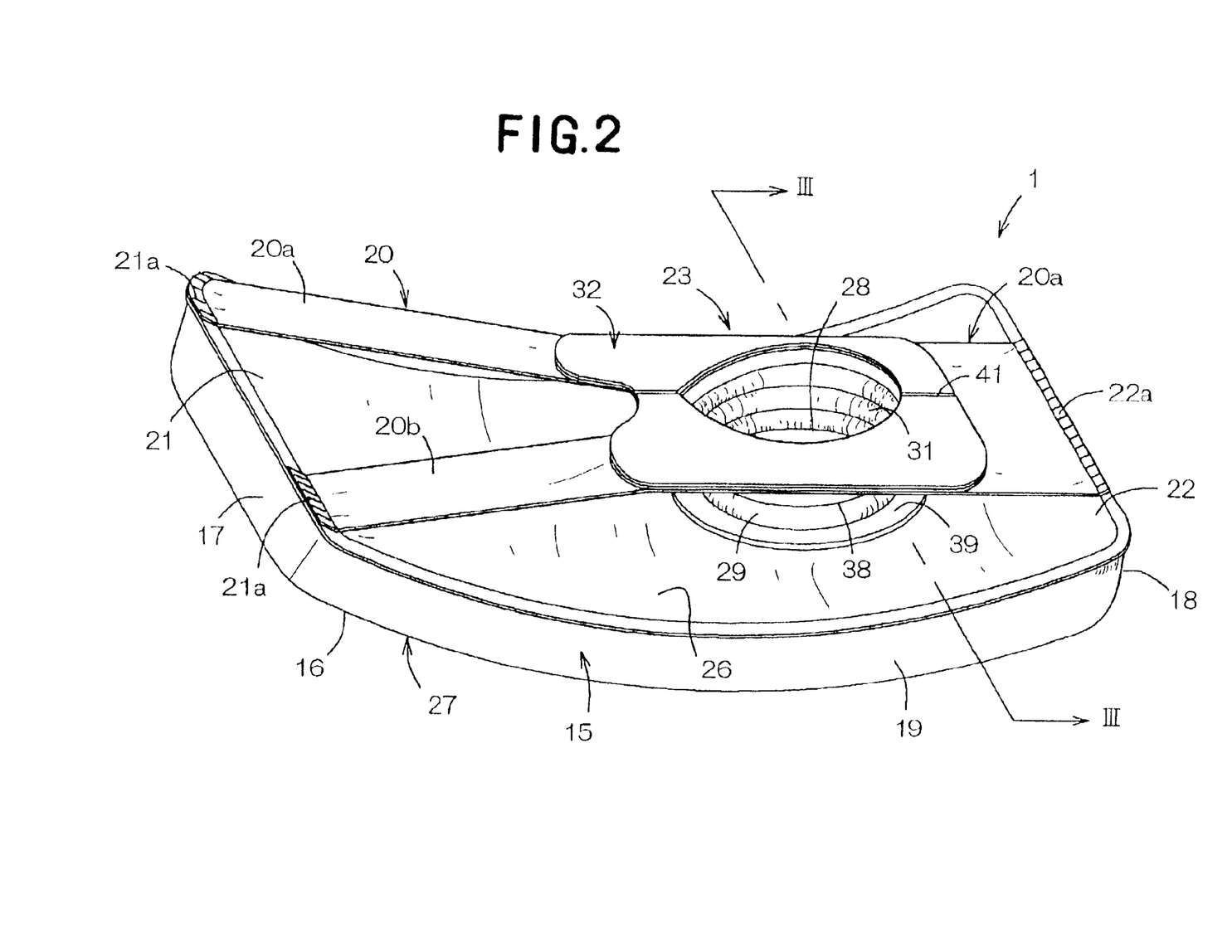
FIG. 2 is a perspective view of the wearing article for disposal of bodily discharges.
Figure 3:
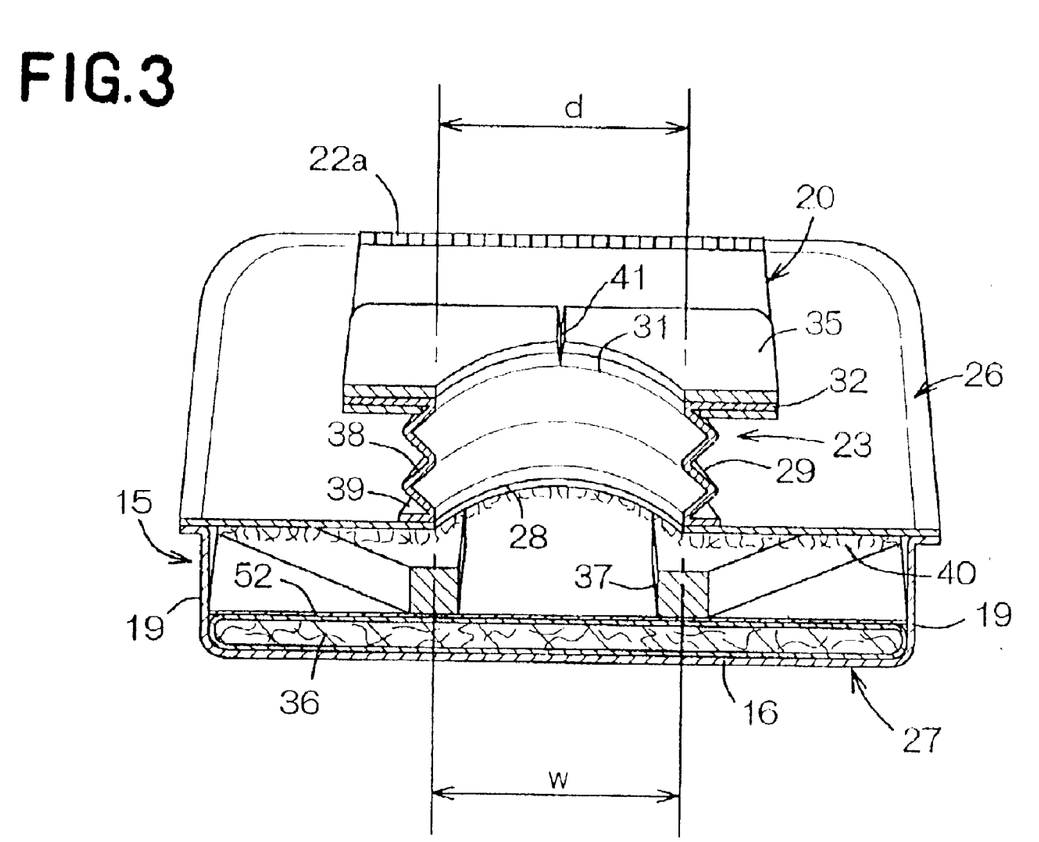
FIG. 3 is a cross-sectional view taken along a line III—III in FIG. 2.

FIG. 2 is a perspective view showing the disposal means I in a state free from any restraint and FIG. 3 is a cross-sectional view taken along a line III—III in FIG. 2. The disposal means 1 has a bag-like loose passage receptacle 15 formed by placing a body facing upper sheet 26 and a garment facing lower sheet 27 which respectively are rectangular, upon each other and adhesively joining or heat-sealing these upper and lower sheets 26, 27 together along peripheral edges thereof, a supporting member 20 extending between the front section 21 and the rear section 22 above the upper sheet 26 and the loose passage inlet 23 vertically extending between the receptacle 15 and the supporting member 20 (See FIG. 1 also).

In the receptacle 15, the upper sheet 26 is formed with an opening 28 and the lower sheet 27 is formed with a bottom 16, front and rear end walls 17, 18 and opposite side walls 19. These bottom 16 and walls 17, 18, 19 define a cavity containing therein a liquid-absorbent layer 36 and a body fluid distributing layer 37.

The loose passage inlet 23 is a means adapted to guide loose passage discharged by the wearer of the disposal means 1 and includes a cylindrical guide 29 extending in vertical direction. The cylindrical guide 29 has its lower end 39 water-tightly joined to a peripheral edge of the opening 28 and its upper end formed with an opening 31 and a flange 32 surrounding this opening 28. The cylindrical guide 29 is inelastically or elastically stretchable in a vertical direction as viewed in FIG. 2 and comprises a cylinder made of a sheet material such as an inelastic nonwoven fabric or a plastic film, or an elastic urethane or a silicone rubber. This cylinder is formed with a plurality of pleats 38 so that the cylinder can be easily stretched and contracted like bellows. The flange 32 formed around the upper end of the cylindrical guide 29 is preferably laminated with a flexible elastic sheet 35 such as a foamed polyethylene sheet, a foamed polyurethane sheet or a nonwoven fabric of crimped fibers so as to come in close contact with the wearer's skin. The flange 32 may be formed on its upper or lower surface in a transversely middle zone of these flange 32 and elastic sheet 35 with a groove 41 extending in the back-and-forth direction to facilitate a vertical deformation of the flange 32.

The supporting member 20 is made of an elastically stretchable material such as an elastically stretchable sheet of urethane rubber, silicone rubber or the like, or an elastically stretchable nonwoven fabric of urethane elastic threads. This supporting member 20 is joined under tension to the front and rear sections 21,22 along marginal edges 21a, 22a thereof as well as to the lower surface of the flange 32 surrounding the loose passage inlet 23. With the disposal means 1 free from any restriction, contraction of the supporting member 20 between the front and rear sections 21,22 causes the receptacle 15 to be curved with the upper sheet 26 inside so that the loose passage inlet 23 may be pulled by the supporting member 20 upward and stretched upward from the upper sheet 26, as will be seen in FIG. 2. Extensibility and stretch stress or tensile stress maybe appropriately adjusted to obtain a desired radius of an arc described by the curved receptacle 15. The cylindrical guide 29 of the loose passage inlet 15 has a sufficient length to ensure that contraction of the supporting member 20 might not be restrained. The supporting member 20 defines a single belt behind the inlet 23 and bifurcates in two branches 20a, 20b in front of the inlet 23 so that the wearer of the disposal means 1 may put his penis between these two branches 20a, 20b of the supporting member 20.

Of the disposal means 1, the upper sheet 26 may be formed by materials selected from a group including a liquid-pervious nonwoven fabric, a liquid-pervious finely apertured plastic film, a liquid-impervious nonwoven fabric and a liquid-impervious plastic film and the lower sheet 27 may be formed by materials such as a liquid-impervious plastic film, more preferably, a breathable and liquid-impervious plastic film. Between the upper and lower sheets 26, 27, there is provided the liquid-absorbent layer 36 comprising water-absorbent material such as fluff pulp and super-absorbent polymer particles covered with a liquid-pervious sheet such as a tissue paper 52. More preferably, the body fluid distributing layer 37 made of a flexible elastic material such as a foamed polyurethane, a foamed polyethylene, a foamed polystyrene or the like is formed on the liquid-absorbent layer 36.

Figure 4:
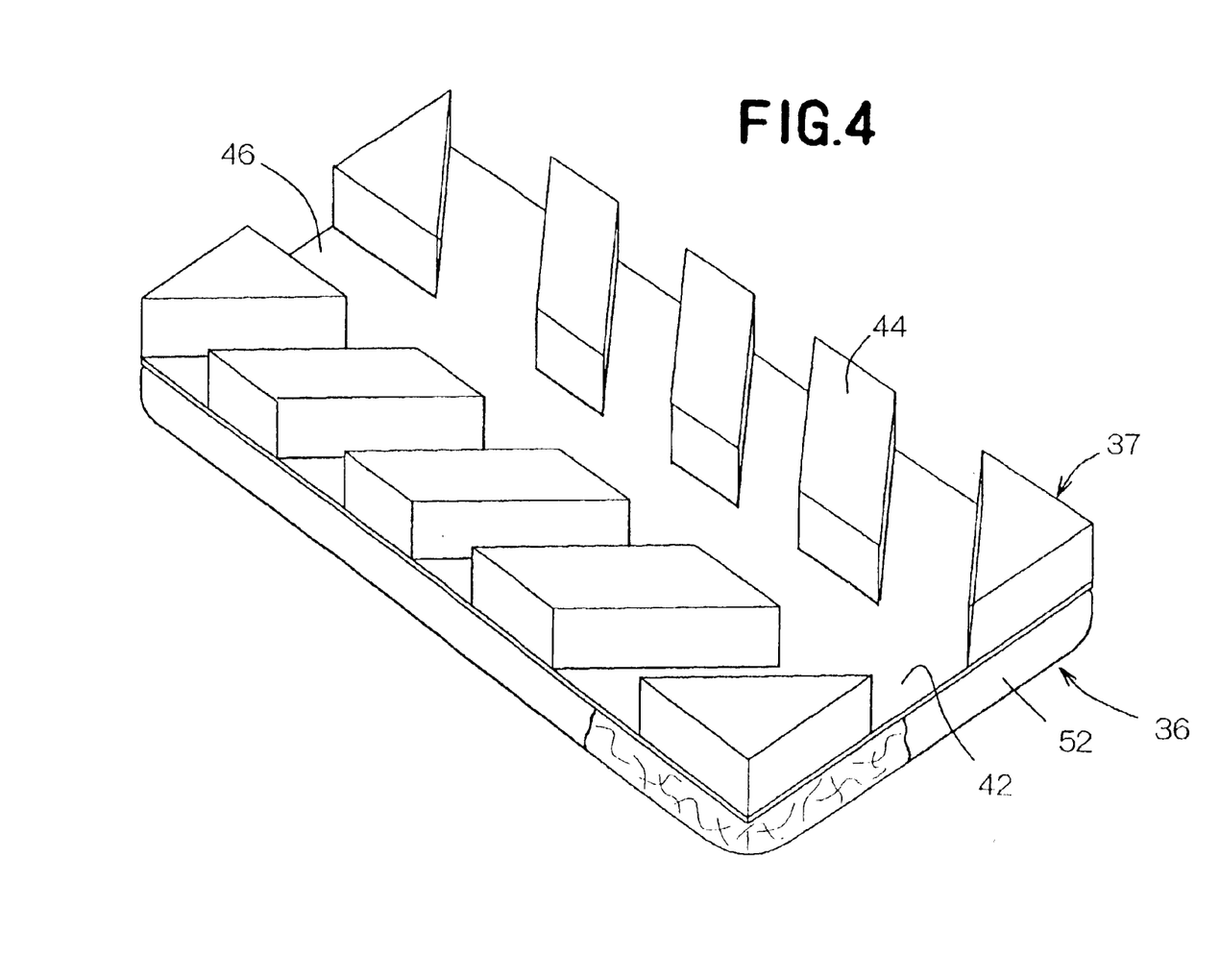
FIG. 4 is a perspective view showing a liquid-absorbent layer and a bodily discharge distributing layer.

FIG. 4 is a perspective view showing the liquid-absorbent layer 36 and the body fluid distributing layer 37 (See FIG. 3) constituting together the receptacle 15 as partially cut-away. The panel-like liquid-absorbent layer 36 comprises fluff pulp or a-mixture of fluff pulp and super-absorbent polymer particles compressed to a desired thickness and covered with the tissue paper 52. The body fluid distributing layer 37 is placed on this liquid-absorbent layer 36. The layer 37 comprises a water-absorbent sheet 42 such as a tissue paper or a net-like water-pervious sheet and a plurality of blocks 44 made of a foamed polyurethane having three-dimensional network structure placed on the water-absorbent sheet or the water-pervious sheet. Between each pair of the adjacent blocks 44, a groove 46 is defined so that loose passage or the like introduced by the cylindrical guide 29 may be distributed by this groove 46 to respective regions of the receptacle 15. The height of the blocks 44 may be appropriately adjusted to space the upper and lower sheets 26, 27 by an appropriate dimension and thereby to facilitate loose passage to flow into the receptacle 15. The respective blocks 44 are joined to the water-absorbent sheet 42 at predetermined relative positions. It should be understood that no restrictions on the configuration or layout of the blocks 44 and the groove 46 are specified. It is also possible without departing from the scope of this invention to use the receptacle 15 without the body fluid distributing layer 37.

When the disposal means 1 having its receptacle 15 curved is worn in combination with the diaper 2 shown in FIG. 1, the opening 31 of the cylindrical guide 29 may be so placed to coincide with the position of a wearer's anus. Contraction of the supporting member 20 serves to move the position of the flange 32 to be in close contact with the zone surrounding the anus and thereby retains the opening 31 in coincidence with the position of the anus. For such disposal means 1, it is unnecessary to previously coat an upper surface of the flange 32 with an adhesive having a high adhesive force by means of which the flange 32 is adhered to a wearer's skin as has been the case with the conventional disposal means. If the flange 32 is coated with an adhesive, it will be possible to alleviate the adhesive force thereof adequately to avoid uncomfortable irritation of a wearer's skin.

The upper sheet 26 of the receptacle 15 in the disposal means 1 is preferably of liquid-pervious so that urine discharged by a wearer may be received by the front section 21 of the disposal means 1 and guided by permeation through the upper sheet 26 into the receptacle 15. To facilitate such permeation, if the upper sheet 26 is made of finely apertured plastic film, the inner surface of the plastic film is preferably lined with a hydrophilic fibrous assembly having a basis weight of 20–50 g /m$^2$. If the upper sheet 26 is formed by a liquid-pervious nonwoven fabric, the inner surface of this nonwoven fabric is preferably lined with a hydrophilic fibrous assembly 40 (See FIG. 3) having a density higher than that of the nonwoven fabric. Such lining facilitates urine to permeate from the outer side of the receptacle 15 into the fibrous assembly 40. If it is unnecessary to incorporate such lining, the liquid-impervious topsheet may be used to implement this invention.

The lower sheet 27 of the receptacle 15 in the disposal means 1 may be coated on a part of its outer surface with an adhesive or provided on such part with a male member of a mechanical fastener commonly known under the trademark "VELCRO" to fasten the disposal means 1 to the topsheet 3 of the diaper 2 in a peelable fashion.

Figure 5:
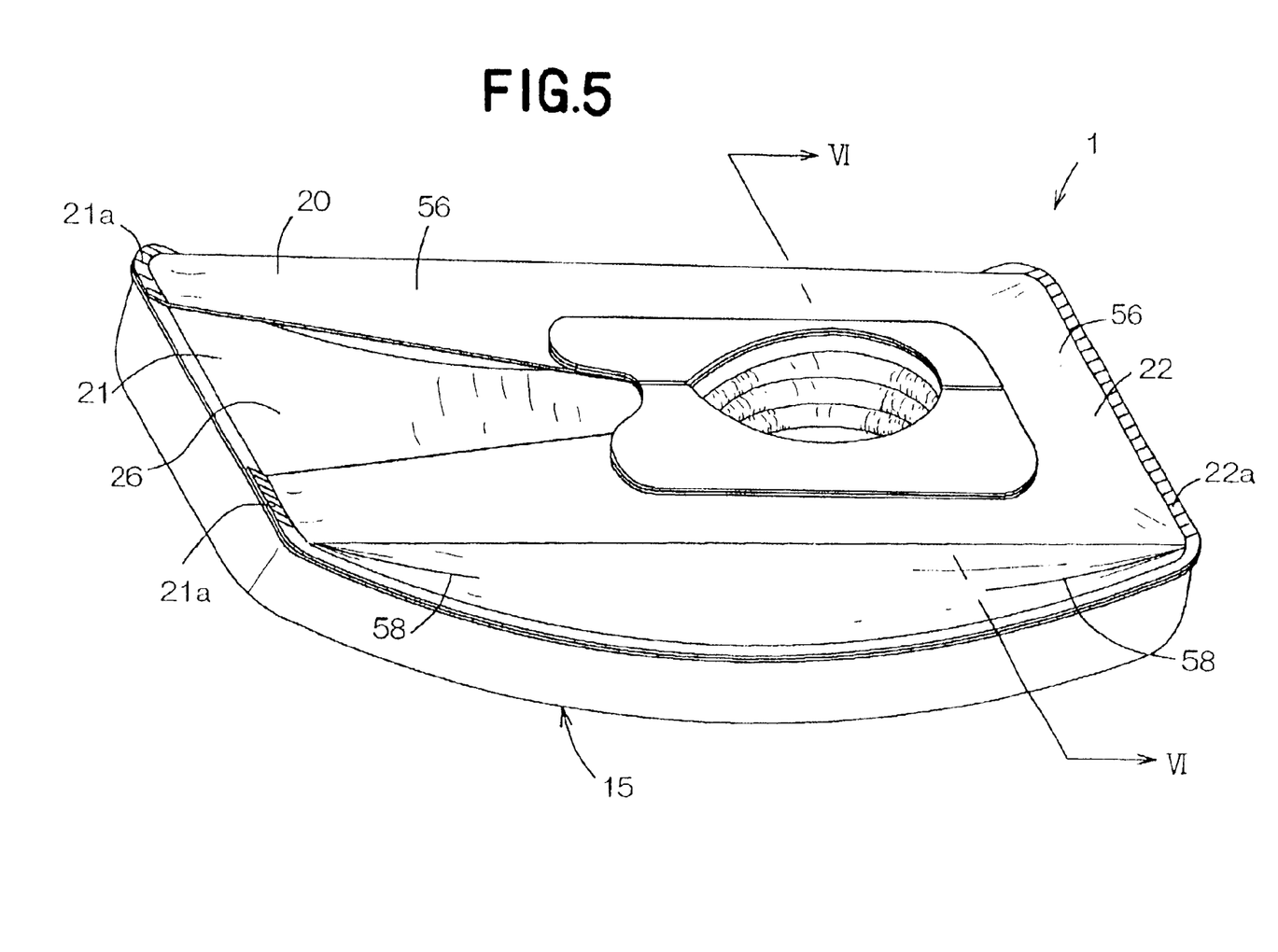
FIG. 5 is a perspective view similar to FIG. 2 but showing another embodiment of this invention.
Figure 6:
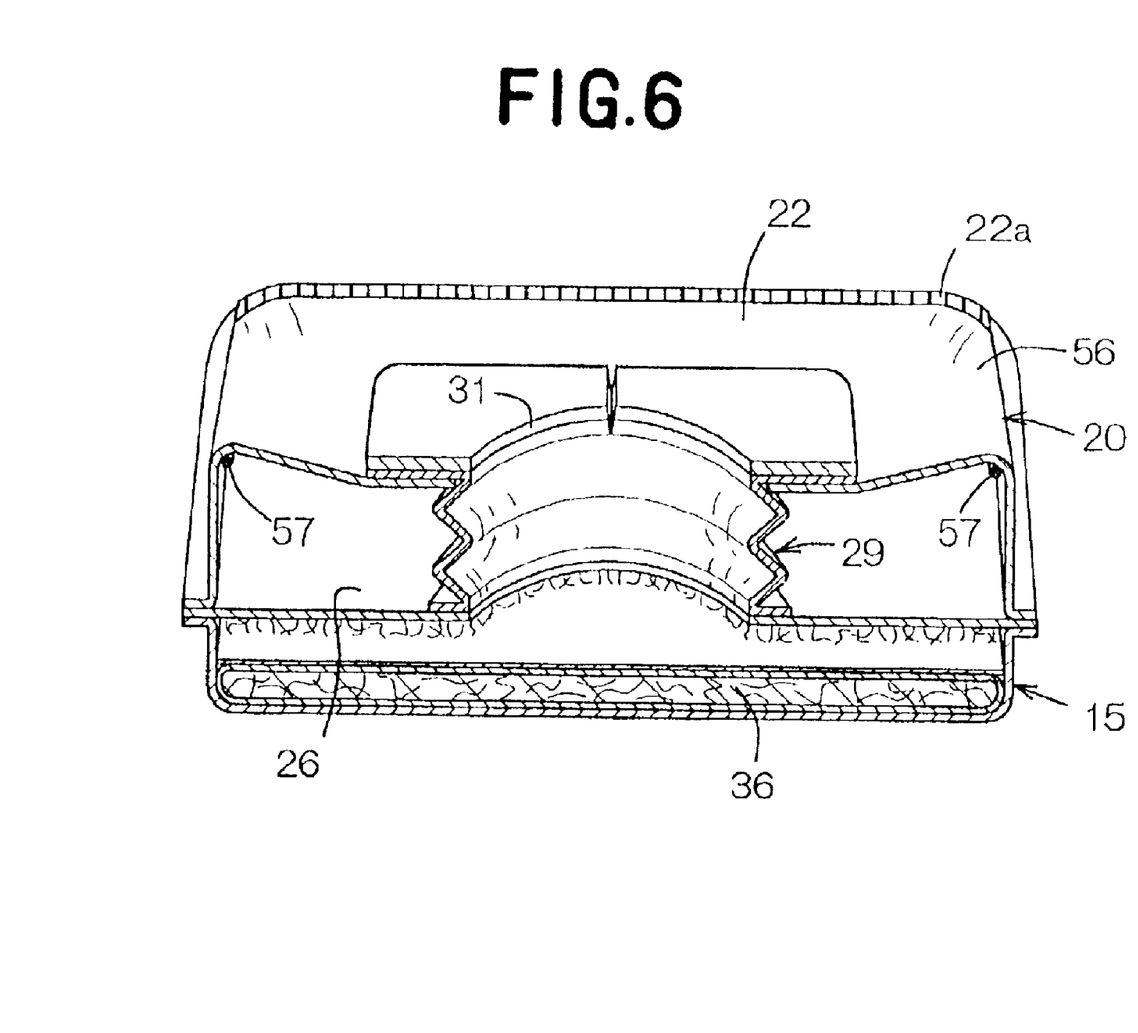
FIG. 6 is a cross-sectional view taken along a line VI—VI in FIG. 5.

FIG. 5 is a perspective view similar to FIG. 2 but showing another embodiment of this invention and FIG. 6 is a cross-sectional view taken along a line VI—VI in FIG. 5. In the case of this disposal means 1, the supporting member 20 is formed of a non-stretchable sheet 56 and string or strand-like elastic members 57. The sheet 56 is liquid-pervious or liquid-impervious and joined to the lower surface of the flange 32 formed along the peripheral edge of the upper end of the inlet 29 and also to the peripheral edge of the receptacle 15. In this manner, the sheet 56 covers more than half the area of the upper sheet 26 of the receptacle 15 as is shown in FIG. 5. In the front section 21 of the receptacle 15, however, the sheet 56 is partially cut away so as to expose the upper sheet 26. The space defined by partially cutting away the sheet 56 may hold a wearer's penis. The sheet 56 is formed with gussets 58 extending along the side edges of the receptacle 15. The elastic members 57 extend along the side edges of the receptacle 15 and are joined to the front and rear sections 21, 22 along the zones 21a, 22a thereof. With the disposal means 1 in a state free from any restriction, contraction of the elastic members 57 causes the receptacle 15 to be curved and, as will be seen in FIG. 6, causes the gussets 58 to be developed. Consequently, the sheet 56 is spaced upward from the upper sheet 26 and thereby the loose passage inlet 23 is stretched upward. Though not shown in FIGS. 5, 6, many gathers are formed on the sheet 56. In the embodiment so arranged that the elastic members 57 are operatively associated with the loose passage inlet 23 by means of the non-stretchable sheet 56, the supporting member 20 facilitates the opening 31 of the loose passage inlet 23 to be retained in coincidence with the position of the anus as the case of the embodiment shown FIGS. 2, 3 in which the supporting member 20 is entirely elastic is directly connected to the loose passage inlet 23. The presence of the sheet 56 prevents urine on the topsheet 26 from leaking outside. The disposal means 1 shown in FIGS. 5, 6 includes the liquid-absorbent layer 36 but not the body fluid distributing layer within the receptacle 15. The sheet 56 may be joined to the elastic members 57.

Figure 7:
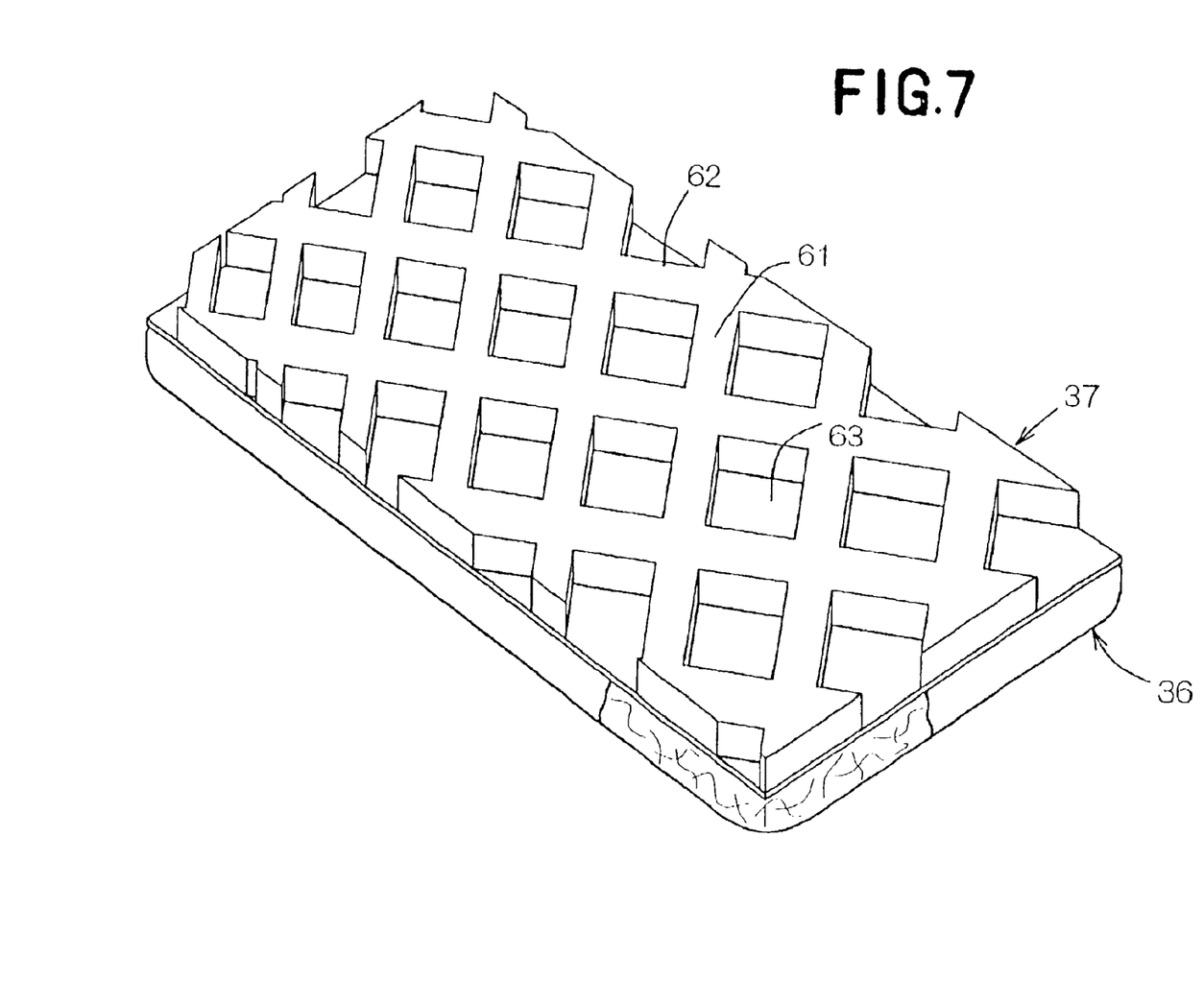
FIG. 7 is a view similar to FIG. 4 but showing still another embodiment of this invention.

FIG. 7 is a view similar to FIG. 4 but showing still another embodiment of this invention. The body fluid distributing layer 37 of the receptacle 15 in this embodiment has a plurality of ridges 61, 62 a formed or flexible elastic material such as a foamed urethane intersecting one another so as to define depressions 63 into which loose passage can flow.

While the disposal means 1 has been described in reference to the drawings to be used in combination with the disposable diaper 2, it should be understood that the diaper 2 is one example of means adapted to hold the disposal means 1 on a wearer's body and the disposal means 1 may be used in combination with a diaper cover or pants. While the disposal means 1 is preferably configurated to be relatively long in back-and-forth direction in a wearer's crotch region, the exterior shape of the disposal means 1 may be realized in appropriate shapes such as an hourglass other than the rectangular shape as in the illustrated embodiments. The term "joining" used herein means that the relevant members are integrated together using appropriate techniques such as adhesion and welding.

The throwaway wearing article for disposal of bodily discharges according to this invention is characterized in that the flat bag is provided with the cylindrical guide for bodily discharge which is elastic in its axial direction and the elastic member extending under tension in back-and-forth direction of the bag is operatively associated with this cylindrical guide in the vicinity of its upper end opening so that contraction of the elastic member may cause the cylindrical guide to be stretched upward and the flange formed around the opening of the cylindrical guide may be brought in close contact with the zone surrounding the anus. In this way, the opening can be retained in coincidence with the position of the anus without fastening the flange to the zone surrounding the anus by means of an adhesive.

What is claimed is:

1. A throwaway wearing article for disposal of bodily discharges comprising a body facing upper sheet, a garment facing lower sheet and an elongated flat bag being composed of a front section formed on a side of a wearer's belly and a rear section formed on a side of said wearer's back wherein said upper sheet is formed with a cylindrical guide means adapted to guide bodily discharges into said bag, said throwaway wearing article for disposal of bodily discharges further comprising:

said cylindrical guide means having a lower end contiguous to an opening formed in said upper sheet and an upper end lying above said upper sheet so that said cylindrical guide means is stretched and contracted in a vertical direction between said upper and lower ends;

said bag being provided with an elastic member extending under tension between said front and rear sections above said upper sheet and further extending at least longitudinally outward from opposite sides of said cylindrical guide means; and said elastic member being operatively associated with a peripheral edge of said upper end of said guide means so that contraction of said elastic member causes said guide means to be stretched upward as said wearing article is curved longitudinally of said bag with said upper sheet inside.

2. The wearing article according to claim 1, wherein said elastic member is operatively associated with the upper end's peripheral edge of said guide means by means of a non-stretchable sheet laying above said upper sheet and joined to a peripheral edge of said bag.

3. The wearing article according to claim 2, wherein said non-stretchable sheet is cut out in the front section of said wearing article so that said upper sheet is exposed in this cutout region.

4. The wearing article according to claim 1, wherein said elastic member bifurcates so as to define a space opening toward the front section of said wearing article and said upper sheet is exposed in said space.

5. The wearing article according to claim 1, wherein said bag is formed by placing an upper sheet and a lower sheet which are joined together along peripheral edges thereof and defining a cavity containing therein a liquid absorbent layer comprising a water-absorbent material.

6. The wearing article according to claim 1, wherein a flange is formed around said upper end of said cylindrical guide means and said flange is laminated with a flexible elastic sheet.

* * * * *